US008186877B2

(12) United States Patent
Klimovitch et al.

(10) Patent No.: US 8,186,877 B2
(45) Date of Patent: May 29, 2012

(54) METHOD AND SYSTEM FOR USING COMMON SUBCHANNEL TO ASSESS THE OPERATING CHARACTERISTICS OF TRANSDUCERS

(75) Inventors: Gleb V. Klimovitch, Santa Clara, CA (US); Timothy E. Ciciarelli, San Jose, CA (US); Shena H. Park, San Francisco, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1156 days.

(21) Appl. No.: 11/967,217

(22) Filed: Dec. 30, 2007

(65) Prior Publication Data

US 2009/0171342 A1 Jul. 2, 2009

(51) Int. Cl.
*G01K 7/00* (2006.01)
(52) U.S. Cl. .......................... 374/170; 374/183
(58) Field of Classification Search ............... 374/170, 374/178, 183
See application file for complete search history.

(56) References Cited

U.S. PATENT DOCUMENTS

| | | | | |
|---|---|---|---|---|
| 4,065,715 | A * | 12/1977 | Jaffe et al. ...................... | 374/183 |
| 4,481,465 | A | 11/1984 | Fredericks et al. | |
| 4,783,659 | A | 11/1988 | Frick | |
| 6,048,094 | A | 4/2000 | Tornare | |
| 6,554,780 | B1 * | 4/2003 | Sampson et al. ............... | 600/587 |
| 6,743,184 | B2 * | 6/2004 | Sampson et al. ............... | 600/560 |
| 6,783,274 | B2 | 8/2004 | Umeyama et al. | |
| 6,872,183 | B2 * | 3/2005 | Sampson et al. ............... | 600/561 |
| 7,063,670 | B2 * | 6/2006 | Sampson et al. ............... | 600/560 |
| 7,252,664 | B2 | 8/2007 | Nasab et al. | |
| 2001/0004236 | A1 * | 6/2001 | Letkomiller et al. .......... | 374/183 |
| 2003/0191412 | A1 * | 10/2003 | Sampson et al. ............... | 600/561 |
| 2004/0215099 | A1 * | 10/2004 | Sampson et al. ............... | 600/560 |
| 2005/0143728 | A1 * | 6/2005 | Sampson et al. ................. | 606/41 |
| 2007/0185680 | A1 | 8/2007 | Kambe et al. | |
| 2009/0149846 | A1 * | 6/2009 | Hoey et al. ...................... | 606/27 |
| 2009/0163909 | A1 * | 6/2009 | Ma et al. .......................... | 606/41 |
| 2009/0171342 | A1 * | 7/2009 | Klimovitch et al. ............ | 606/34 |

(Continued)

OTHER PUBLICATIONS

PCT International Search Report and Written Opinion of the International Searching Authority for PCT/US08/84296 dated Jan. 26, 2009.

*Primary Examiner* — Yaritza Guadalupe-McCall
(74) *Attorney, Agent, or Firm* — Wiley Rein LLP

(57) ABSTRACT

A system and method for using a common subchannel to assess operating characteristics of one of a plurality of transducers that are coupled to said subchannel is disclosed. The plurality of transducers are divided into subsets and each subset is coupled to a subchannel. The system is configured to activate a selected transducer on the subchannel and the subchannel delivers operational information on the activated transducer. The present invention reduces the number of subchannels required to collect information on the plurality of transducers. The present invention may utilize one or more loading conditions to take at least one measurement, which at least one measurement is then used to derive operational information on the transducer. In one configuration, information on the amount of energy being delivered to the transducer is collected simultaneously with information on the operating temperature. In another embodiment only the temperature is measured. The present invention permits a more compact ablation device to be constructed based on the invention's ability to reduce the total number of subchannels required to collect transducer information.

27 Claims, 5 Drawing Sheets

U.S. PATENT DOCUMENTS

2009/0209950 A1* 8/2009 Starksen .......................... 606/21
2010/0198214 A1* 8/2010 Layton et al. ................... 606/33
2010/0262133 A1* 10/2010 Hoey et al. ...................... 606/27
2010/0274238 A1* 10/2010 Klimovitch ..................... 606/33
2011/0291736 A1* 12/2011 Klimovitch et al. .......... 327/365

* cited by examiner

METHOD AND SYSTEM FOR USING COMMON SUBCHANNEL TO ASSESS THE OPERATING CHARACTERISTICS OF TRANSDUCERS

BACKGROUND OF THE INVENTION a. Field of the Invention

The instant invention generally relates to devices and methods for treating electrophysiological diseases of the heart. In particular, the instant invention relates to devices and methods for controlling and monitoring epicardial ablation for the treatment of atrial fibrillation.

b. Background Art

It is well known that atrial fibrillation results from disorganized electrical activity in the heart muscle (the myocardium). The surgical maze procedure has been developed for treating atrial fibrillation, and involves the creation of a series of surgical incisions through the atrial myocardium in a preselected pattern so as to create conductive corridors of viable tissue bounded by scar tissue.

As an alternative to the surgical incisions of the maze procedure, transmural ablations of the heart may be used. Such ablations may be performed either from within the chambers of the heart (endocardial ablation), using endovascular devices (e.g., catheters) introduced through arteries or veins, or from outside the heart (epicardial ablation) using devices introduced into the patient's chest. Various ablation techniques may be used, including, but not limited to, cryogenic ablation, radio frequency (RF) ablation, laser ablation, ultrasonic ablation, and microwave ablation. The ablation devices are used to create elongated transmural lesions—that is, lesions extending through a sufficient thickness of the myocardium to block electrical conduction—forming the boundaries of the conductive corridors in the atrial myocardium. Perhaps most advantageous about the use of transmural ablation rather than surgical incision is the ability to perform ablation procedures without first establishing cardiopulmonary bypass (CPB).

In performing the maze procedure and its variants, whether using ablation or surgical incisions, it is generally considered most efficacious to include a transmural incision or lesion isolating the pulmonary veins from the surrounding myocardium. The pulmonary veins connect the lungs to the left atrium of the heart, joining the left atrial wall on the posterior side of the heart.

This location creates significant difficulties for endocardial ablation devices for several reasons. First, while many of the other lesions created in the maze procedure can be created from within the right atrium, the pulmonary venous lesions must be created in the left atrium, requiring either a separate arterial access point or a transeptal puncture from the right atrium. Second, the elongated and flexible endovascular ablation devices are difficult to manipulate into the complex geometries required for forming the pulmonary venous lesions and to maintain in such positions against the wall of the beating heart. This is very time-consuming and can result in lesions that do not completely encircle the pulmonary veins or that contain gaps and discontinuities. Third, because elongated ablation devices are often pre-shaped to maintain a minimum curvature, a surgeon must create an incision in the patient's body sufficiently large to accommodate not only the width of the ablation device, but also its curvature. Finally, the heat generated by endocardial devices that flows outward through the myocardium cannot be precisely controlled and can damage extracardiac tissues such as the pericardium, the phrenic nerve and other structures.

What are needed, therefore, are devices and methods for forming lesions that isolate the pulmonary veins from the surrounding myocardium that overcome these problems. The devices and methods will preferably be utilized epicardially to avoid the need for access into the left chambers of the heart and to minimize the risk of producing thrombus.

Additional aspects of the present invention are directed to devices and methods for ablating tissue. Ablation of heart tissue and, specifically, ablation of tissue for treatment of atrial fibrillation is developed as a particular use of these other aspects of the present invention.

BRIEF SUMMARY OF THE INVENTION

It is desirable to be able to reduce the size of the ablation devices being inserted into the patient's body.

It is also desirable to reduce the number of electrical busses being used in the ablation devices.

It is also desirable to utilize temperature sensors for each ablation element used in the ablation device to provide more complete information on the performance of the ablation procedure.

It is therefore desirable to be able to provide an ablation device for forming pulmonary vein isolation lesions that can be introduced through a relatively small incision.

It is further desirable to provide an ablation device for facilitating formation of a substantially continuous lesion about the pulmonary veins.

It is also desirable to provide an ablation device that may be used epicardially in order to avoid the need for access into the left chambers of the heart and to minimize the risk of producing thrombi.

According to an embodiment, a method of using a common subchannel to assess operating characteristics of one of a plurality of transducers that are coupled to said subchannel is disclosed. A plurality of transducers and a plurality of sensors are provided. Each of the plurality of transducers has one of the plurality of sensors coupled thereto for determining the temperature of the transducer, and each transducer is configured to be selectively powered with RF energy. An output of each of the plurality of sensors is connected to a subchannel, and the subchannel has a measurement terminal on one end and a coupling input on the other end. The measurement terminal is configured for connecting to a meter, and the coupling input is configured to be coupled to an output of each of the plurality of sensors. A RF power source is connected to a selected one of the plurality of transducers, which selectively provides a low frequency power source to the sensor coupled to the selected transducer. At least one voltage is measured on the measurement terminal, which is then used to determine the temperature of the sensor coupled to the selected transducer. Additional measurements may be taken. For example, a measurement may be made of a first voltage level representative of a voltage that is being applied to the sensor coupled to the selected transducer, and then a measurement may be made of a second voltage level representative of a current that is flowing through the sensor coupled to the selected transducer. These two measurements may be used to calculate the resistance of the sensor using Ohms law, and then the resistance may be used to derive the temperature of the sensor using a known relationship between temperature and resistance for the sensor to determine the temperature of the sensor. Various circuits may be used that rectify and filter the RF power source connected to the selected transducer. In addition, voltage divider circuit may be used to condition the RF power source connected to the selected transducer, and the conditioned signal may then be rectified and filtered with a low pass filter to selectively provide a low frequency power source to the selected sensor. Optionally, voltage regulators may be used to provide a power source to the sensor.

In a variation, each of the plurality of transducers may be configured to operate at a different frequency, for example, by using a resonant frequency circuit. Then the RF power source may be tuned to the resonant frequency of a particular transducer, which will selectively power the transducer and selectively provide information on its operation.

The present invention can be used to provide power information regarding the operation of a transducer (e.g., information on the amplitude of the RF power being delivered) as well as temperature information. In some configurations, the present invention will provide just temperature information on the operation of the transducer. Various sensors may be used, but preferably, the sensor is a thermistor. Other sensors may be used to provide temperature information, for example, provided there is a known relationship between temperature and some parameter that may be measured (such as voltage, current and/or resistance).

According to another aspect of the invention, a method of using a common subchannel to assess characteristics of one of a plurality of transducers that are coupled to said subchannel is provided. A plurality of transducers is provided, each of which may be selectively powered using RF power. A sensor is then coupled to each of said plurality of transducers. An output of each of the sensors is connected to a subchannel that has a measurement terminal on one end and a coupling input on the other end. The measurement terminal is configured for connecting to an analog meter, and the coupling input is configured to be coupled to an output of each of the plurality of sensors. The RF power source may be selectively delivered to one of the plurality of transducers, and an output of the RF power source, at the input to a transducer, may be low pass filtered to provide low-frequency power to the sensor coupled to the transducer receiving RF power. A voltage may be measured on the measurement terminal, and then the measured at least one voltage may be used to characterize the operation of the sensor. For example, a first measurement may be made of a voltage level representative of a voltage that is being applied to the sensor coupled to the transducer that is receiving RF power. A second measurement may be made of a voltage representative of a current that is flowing through the sensor coupled to the transducer that is receiving RF power. The resistance of the sensor may be calculated using these measurements, and then based on the resistance, a temperature may be derived using the known relationships between resistance and temperature for the particular sensor being used. Rectification circuits may be used to convert the RF energy into a low frequency voltage.

In yet another embodiment of the invention, an ablation system is disclosed. The system has a plurality of transducers, divided into a number N of subsets, N being less than a total number of the plurality of transducers. The system also has a controller configured to activate no more than one transducer at a time in each subset of transducers. The system also has N subchannels for transmitting electrical information, each of the N subchannels being coupled to a respective subset of the N subsets of transducers. There are a plurality of detector circuits, each of the plurality of detector circuits being coupled to one of the plurality of transducers, and each of the plurality of detector circuits includes a sensor. There is also a measurement device for measuring an analog signal present on one of the N subchannels. The controller uses an output from the measurement device to assess information being measured by the sensor coupled to a transducer that has been activated by the controller. The system may also include a switching network to selectively couple one of the N subchannels to the measurement device for measurement. The system may measure a first voltage level representative of a voltage that is being applied to the sensor coupled to the activated transducer and then measure a second voltage level representative of a current that is flowing through the sensor coupled to the activated transducer. The controller can use this information to derive a temperature of the sensor coupled to the activated transducer.

According to still another embodiment, a measurement system for monitoring a plurality of transducers using a common measurement subchannel is provided. The system includes: a plurality of transducers, each of which is coupled to an RF power source; an RF controller to control the delivery of RF power to the plurality of transducers, configured such that no more than one of the plurality of transducers is powered at any point in time; and a plurality of detector circuits coupled to the plurality of transducers. Each of the plurality of detector circuits is associated with one of the plurality of transducers, and each of the plurality of detector circuits includes: a rectification circuit to rectify an RF power signal applied to the coupled transducer; a low pass filter to filter the rectified signal; a sensor; and an output port to present a low frequency detected signal as measured relative to the sensor. A common measurement subchannel is coupled to each output port of the plurality of detector circuits. The system may also include a measurement selection circuit to permit the system to measure the output of the sensor under different loading conditions. A switch is used to change the loading conditions. The loading conditions can facilitate measurement of the voltage and/or current associated with the sensor, and then the measurement information can be used to derive operational information on the transducer being activated.

The preferred sensor is a thermistor whose resistance varies as a function of temperature, but other sensors may be used. Various circuitry may be used to pre-condition and/or filter the circuits, including various combinations of diodes, resistors, capacitors, zener diodes, inductors and capacitors.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
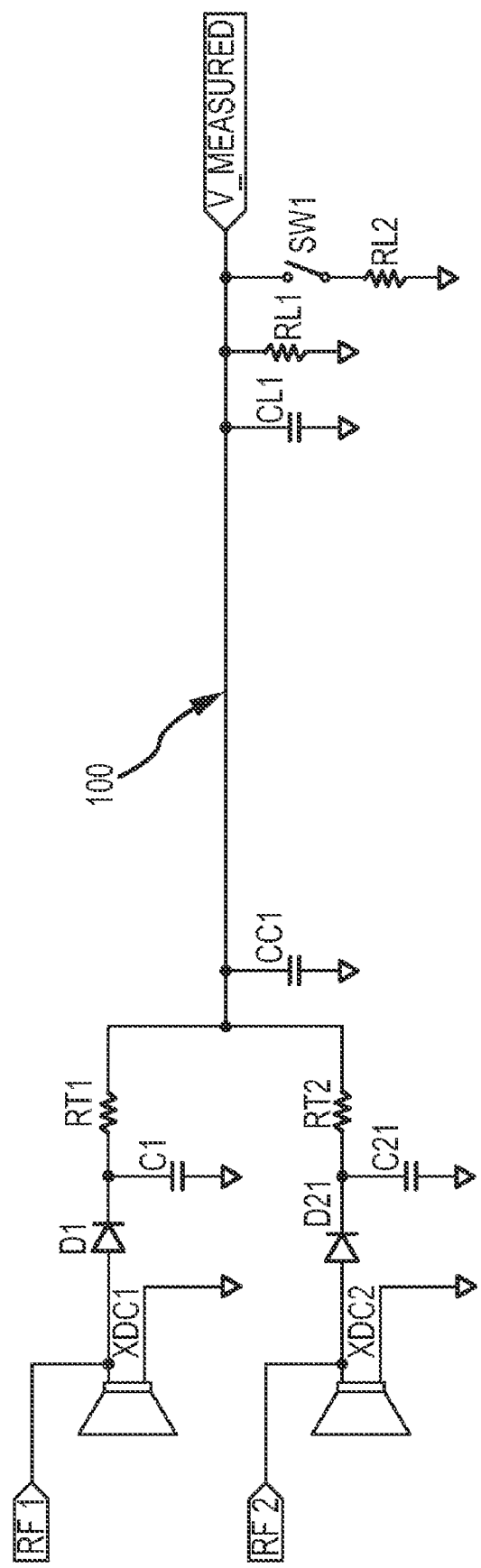
FIG. 1 is circuit diagram for an embodiment of the present invention.

The present invention provides a method and system for assessing the operating characteristics of a plurality of transducers, and in particular, permits the monitoring of operating information using a reduced number of subchannels.

The present invention utilizes a plurality of high intensity focused ultrasound ("HIFU") or other transducers that deliver ablation energy to the myocardium so as to create transmural lesions of sufficient depth to block electrical conduction. Preferably, the transducers are arranged on a belt-like device that is placed around a patient's atrium and the transducers deliver HIFU energy to targeted tissue areas to create a uniform, continuous, linear lesion.

An advantage of using ultrasound transducers for ablating tissue is that the transducers may be used for other measurements. For example, the transducer may be used to provide information on tissue thickness, thickness of fat or muscle layers, and blood velocity data. The ultrasound transducer may also be used to assess the adequacy of contact between the device and the tissue to be ablated. These features find obvious use in the methods described herein and all uses of ultrasound mentioned here, such as temperature feedback control, may be accomplished using other methods and devices.

The present invention is also designed to utilize transducers other than HIFU transducers, including, for example, RF electrodes, microwave transmitters, cryogenic elements, lasers, heated elements, as well as hot fluid or other types of ablation elements suitable for forming transmural lesions.

Preferably, the transducers are positioned so as to facilitate lesion formation on the three-dimensional topography of the left atrium. For example, lateral electrodes face medially to permit ablation of the myocardium on the lateral side of the left inferior pulmonary vein and medial electrodes anteriorly to permit ablation of the posterior surface of the myocardium adjacent to the left inferior pulmonary vein.

In the operation of the transducers, it is desired to measure the electrical power being delivered to the transducer, as well as to monitor the temperature of the transducer. Temperature measurements are preferably performed at or near the transducer location, meaning that the temperature sensors are located at or near the transducer location. The temperature information must then be communicated to the control system that controls and powers the transducers, and such communications can be a challenge in the presence of strong high frequency interference (especially when the transducers are powered with RF energy). With respect to the sensors that are described herein as "coupled" to the transducer, the use of the term "coupled" is intended to describe that the sensor is located at or near the transducer, or sufficiently close to the tissue, such that the sensor provides meaningful information about the operation of the transducer. Thus, "coupled" encompasses both electrical connection and proximity.

Digitally communicating the temperature information is problematic for many reasons. Digital communication techniques can be sensitive, especially in the presence of strong high frequency interference. Using a temperature sensor that communicates digitally may also utilize sensors that are bulky, which may adversely impact the size of an ablation device. Generally, it is desired to decrease the size of ablation devices so that they may be more easily manipulated in difficult areas such as the heart, and a smaller ablation device may also permit a smaller sized incision to be made in a patient's body wherein the ablation device may be inserted.

Because of the problems associated with using digital communications in an environment with high interference, it is generally desirable to use analog communications to transmit temperature information detected by temperature sensors.

Since it is preferable to have at least one temperature sensor associated with each ablation element, there may be a significant number of communication lines (or subchannels) connected to the temperature sensors. In the prior art, analog subchannels cannot be simultaneously shared by multiple transducers, which means that each temperature sensor must have its own subchannel, and since each transducer should have at least one temperature sensor, using a large number of sensors becomes problematic for most ablation devices. The additional wires associated with the operation of so many temperature sensor may increase significantly the size of the catheter.

The present invention solves the problems associated with having to provide a separate subchannel for each temperature sensor being used.

The present invention permits multiple transducers to share a single subchannel, which results in significant reduction in the total number of analog subchannels required in a multiple transducer ablation device. This can significantly reduce the size of the ablation device. In the present invention, only those transducers that are being powered communicate information about their received power levels and their operating temperature. The configurations of the present invention also obviate the need to sequentially connect and disconnect the multiple transducers that share a common subchannel, provided that no more than one transducer on a given subchannel is powered at any time. For example, if 16 transducers are utilized in an ablation device, and each transducer has its own temperature sensor, 16 separate subchannels would be required. With the present invention, if 4 ablation devices share a common subchannel, then the 12 subchannels may be eliminated, leaving 4 separate subchannels, each of which is shared by 4 transducers. If 8 transducers are permitted to share a common subchannel, then 14 subchannels may be eliminated—which may eliminate as many as 28 wires from the ablation device, significantly reducing its size.

The present invention uses the low-frequency domain to measure temperature information and communicate the same to the control system. Low frequency filters can be used to filter the high frequency interference from both the transmitter (that is, the temperature sensor) and the receiver (the system controller that measures the temperature information). This configuration also avoids the requirements for RF shielding that would otherwise be typically required for digital communications.

The device and method of the present invention also provides an output signal that has a sufficiently high voltage amplitude that produces a rather large signal to noise ratio ("SNR"), which is important given the high level of potential high frequency interference. The high SNR also reduces the need for RF shielding that would otherwise be needed to help compensate for the interference.

In addition to providing temperature information, the present invention permits the control system to monitor of the amount of ablation energy being delivered to an active transducer.

An embodiment of the present invention will now be described in connection with the electrical circuit depicted in FIG. 1. The ablation device of the present invention preferably consists of a plurality of transducers that deliver ablation energy, with the plurality of transducers being divided into multiple subsets such that each subset of transducers shares a common communication buss (or "subchannel"). FIG. 1 represents the circuit for one such subset of transducers. Again, the circuit of FIG. 1 may be replicated for each subset of transducers that shares a common subchannel.

While the circuit in FIG. 1 depicts only two transducers (XDC1 and XDC2) sharing a common subchannel, the circuit may be extrapolated to include any number of transducers. Only one transducer on the common subchannel is powered at any given time, regardless of whether the circuit contains two or more transducers. While the operation of the circuit will be described in connection with transducer XDC1, the same functional description will apply equally to transducer XDC2—or any other transducer that may be added to the subchannel. For ease of description, however, the functionality will be discussed only in conjunction with transducer XDC1. Based on this description, it will be understood that if RF power is delivered to transducer XDC2 instead of XDC1, the control system would provide information on sensor RT2.

When an RF energy source (not shown) is connected to RF port RF1, high frequency energy is delivered to the transducer XDC1. Diode D1 rectifies the RF signal, and capacitor C1 serves as a low pass filter to provide a low frequency voltage to sensor RT1. The resulting low frequency signal is delivered by common subchannel 100 to control system (not shown). The combination of diode D1, capacitor C1 and sensor RT1 serve collectively as a detector to provide the control system (not shown) with information on the operation of the transducer. The low frequency signal is preferably further filtered using capacitor CL1 which is physically located at or near the control system and serves to help filter any RF interference that may have been picked up on the subchannel 100. Preferably, a second capacitor CC1 is used on the opposite end of subchannel 100, at or near the point where the outputs of the various sensors are joined to the common subchannel 100, to also assist in removing interference on the subchannel 100.

The control system is configured to make multiple measurements, including measurements under at least two separate loading conditions. With switch SW1 open, the control system measures the output voltage 120. In this loading condition, resistor RL1 and the resistance associated with sensor RT1 serve as a voltage divider. Preferably the resistance of resistor RL1 is substantially greater than the resistance of sensor RT1, and more preferably the resistance of resistor RL1 is at least 10 times greater than the resistance of sensor RT1. Provided the resistance of resistor RL1 is significantly greater than the resistance of sensor RT1, then the measured output voltage approximates the voltage being delivered to the sensor. This measured output voltage may then be used to help characterize the amount of RF energy being delivered to transducer XDC1.

The control system then measures the output voltage under a second loading condition, namely, with the switch SW1 closed. Once switch SW1 is closed, then resistor RL1 is placed in parallel with resistor RL2. Preferably, the resistance of resistor RL2 is substantially less than the resistance of resistor RL1, and more preferably the resistance of resistor RL2 is no more than 1/10 of the resistance of sensor RT1. If the resistance of resistor RL2 is substantially greater than the resistance of resistor RL1, then the measured voltage may be used in connection with the known resistances of resistors RL1 and RL2 to estimate the current that is passing through sensor RT1 using Ohm's Law (V=I*R).

Using these two loading conditions, the control system is able to determine the voltage being applied to the sensor RT1 using the open switch condition (which voltage level may also be used to characterize the ablation power being delivered to the transducer XDC1), as well as the current that is passing through sensor RT1 using the closed switch condition. Using Ohm's law, the resistance associated with the sensor RT1 can be calculated, and in turn, used to determine the temperature at or near the transducer.

Preferably, the sensor RT1 is a thermistor, which generally has a predictable relationship between resistance and temperature. It is contemplated by the present invention that other known sensors may be used provided there is a known relationship between the resistance of the device and its temperature.

To obtain stronger readings of low frequency current, sensors having low thermistor resistances may be used in the circuit, resulting in higher current generation, and in turn, an increased SNR. Preferably, when low thermistor resistances are used, fast measurements are utilized, especially under the closed switch condition. Fast measurements will help to avoid the condition of sensor RT1 self-heating.

While FIG. 1 presents an exemplary detection circuit, one of skill will appreciate that other circuits may be used, including additional diodes, capacitors and resistors.

Further, one of skill in the art will be able to select the components based upon the functional needs of the ablation device, and more particularly, one of skill will understand that the selection of the components of the exemplary circuit shown in FIG. 1 will be based upon factors such as the frequency of the RF power being used in the system, the type of transducers being used for ablation and the type of sensors that are being used to monitor the transducers. By way of example only, where the RF being used ranges from 3 MHz to 7 MHz, the transducers being used are HIFU, and the sensors being used are thermistors whose resistance varies with temperature from about 1.5 K Ohms to about 7.2 K Ohms, the following criteria may be used to select some of the components: RL1 may be selected in the range of about 72 K Ohms to about 100 K Ohms; RL2 may be selected in the range of about 75 Ohms to about 150 Ohms; and each of the capacitors C1, C21, CC1 and CL1 may be selected in the range from about 0.01 uF to about 0.1 uF.

Figure 2:
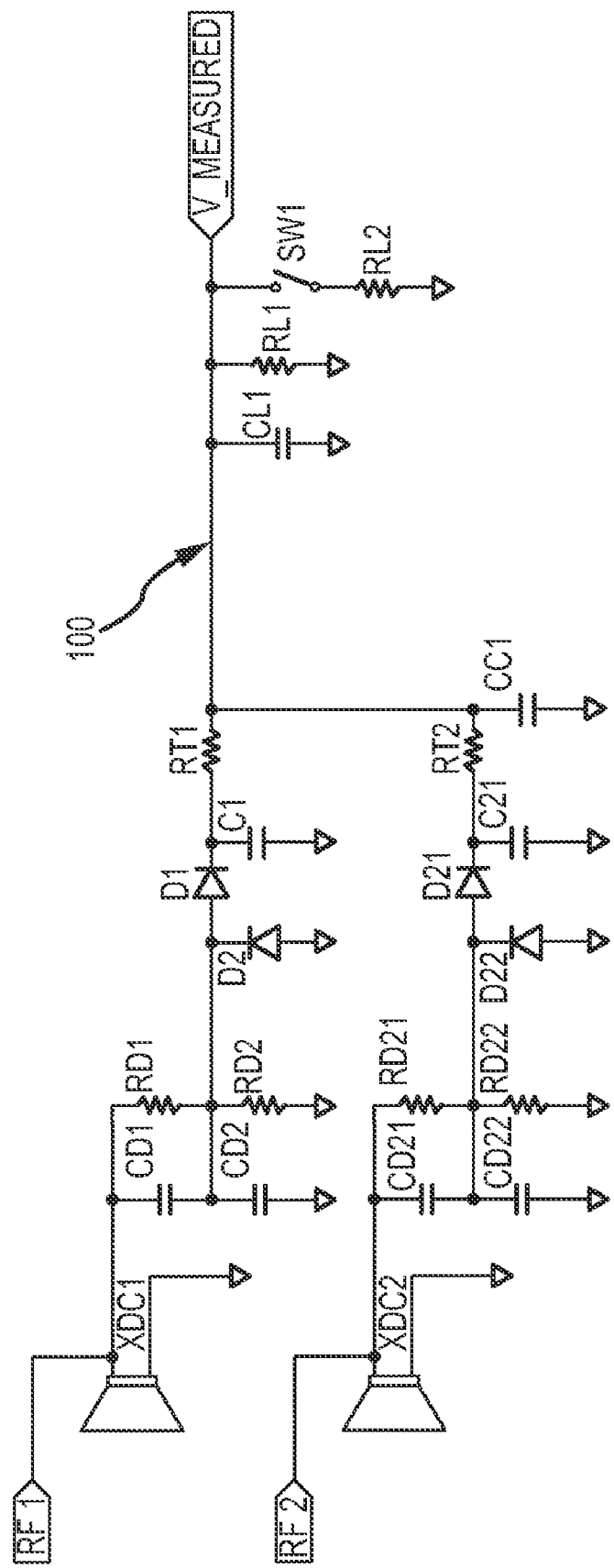
FIG. 2 is circuit diagram for another embodiment of the present invention.

Another embodiment of the present invention will now be described in connection with the electrical circuit depicted in FIG. 2. The ablation device of this embodiment preferably consists of a plurality of transducers that deliver ablation energy, with the plurality of transducers being divided into multiple subsets such that each subset of transducers share a common communication buss (or "subchannel"). FIG. 2 represents the circuit for one such subset of transducers. Again, the circuit of FIG. 2 may be replicated for each subset of transducers that shares a common subchannel.

While the circuit in FIG. 2 depicts only two transducers (XDC1 and XDC2) sharing a common subchannel, the circuit may be extrapolated to include any number of transducers. Only one transducer is powered at any given time, regardless of whether the circuit were to contain two or more transducers. While the operation of the circuit will be described in connection with transducer XDC1, the same functional description will apply equally to transducer XDC2—or any other transducer that may be added to the subchannel. For ease of description, however, the functionality will be discussed only in conjunction with transducer XDC1. Based on this description, it will be understood that if RF power is delivered to transducer XDC2 instead of XDC1, the control system would provide information on sensor RT2.

When an RF energy source (not shown) is connected to RF port RF1, high frequency energy is delivered to the transducer XDC1. The combination of capacitors CD1, CD2 and resistors RD1, RD2 may be used as a voltage divider to pre-condition the RF signal. The pre-conditioned signal may then be delivered to a rectification circuit including diodes D1, D2. One of will appreciate that other rectification circuits may be used, as well as other pre-conditioning circuits. Diode D2 allows for higher resistance values of resistors RD1 and RD2, thereby reducing RF power losses in this resistive divider The rectified and conditioned signal is then delivered to capacitor C1 that serves as a low pass filter to provide a low frequency voltage to sensor RT1. The output from sensor RT1 is then delivered by common subchannel 100 to control system (not shown). The combination of diodes D1, D2, capacitor C1 and sensor RT1 (as well as the preconditioning circuitry) serve collectively as a detector to provide the control system (not shown) with information on the operation of the transducer. The low frequency signal is preferably further filtered using capacitor CL1 that is physically located at or near the control system and serves to help filter any RF interference that may have been picked up on the subchannel 100. Preferably, a second capacitor CC1 is used on the opposite end of subchannel 100, at or near the point where the outputs of the various sensors are joined to the common subchannel 100, to also assist in removing interference on the subchannel 100.

The control system is configured to make multiple measurements, including measurements under at least two separate loading conditions. With switch SW1 open, the control system measures the output voltage 120. In this loading condition, resistor RL1 and the resistance associated with sensor RT1 serve as a voltage divider. Preferably the resistance of resistor RL1 is substantially greater than the resistance of sensor RT1, and more preferably the resistance of resistor RL1 is at least 10 times greater than the resistance of sensor RT1. Provided the resistance of resistor RL1 is significantly greater than the resistance of sensor RT1, then the measured output voltage approximates the voltage being delivered to the sensor. This measured output voltage may then be used to help characterize the amount of RF energy being delivered to transducer XDC1.

The control system then measures the output voltage under a second loading condition, namely, with the switch SW1 closed. Once switch SW1 is closed, then resistor RL1 is placed in parallel with resistor RL2. Preferably, the resistance of resistor RL2 is substantially less than the resistance of resistor RL1, and more preferably the resistance of resistor RL2 is no more than 1/10 of the resistance of sensor RT1. If the resistance of resistor RL2 is substantially greater than the resistance of resistor RL1, then the measured voltage may be used in connection with the known resistances of resistors RL1 and RL2 to estimate the current that is passing through sensor RT1 using Ohm's Law (V=I*R).

Using these two loading conditions, the control system is able to determine the voltage being applied to the sensor RT1 using the open switch condition (which voltage level may also be used to characterize the ablation power being delivered to the transducer XDC1), as well as the current that is passing through sensor RT1 using the closed switch condition. Using Ohm's law, the resistance associated with the sensor RT1 can be calculated, and in turn, used to determine the temperature at or near the transducer.

Preferably, the sensor RT1 is a thermistor, which generally has a predictable relationship between resistance and temperature. It is contemplated by the present invention that other known sensors may be used provided there is a known relationship between the resistance of the device and its temperature.

Yet another embodiment of the present invention will now be described in connection with the electrical circuit depicted in FIG. 3. In this embodiment, instead of measuring both the thermistor temperature and the amplitude of the RF voltage, the circuit of FIG. 1 or 2 may be modified to permit the measurement of temperature only—either by measuring output voltage or current—but not both.

The ablation device of this embodiment preferably consists of a plurality of transducers that deliver ablation energy, with the plurality of transducers being divided into multiple subsets such that each subset of transducers shares a common communication buss (or "subchannel"). FIG. 3 represents the circuit for one such subset of transducers. Again, the circuit of FIG. 3 may be replicated for each subset of transducers that shares a common subchannel.

While FIG. 2 presents an exemplary detection circuit, one of ordinary skill will appreciate that other circuits may be used, including additional diodes, capacitors and resistors.

Further, one of skill in the art will be able to select the components based upon the functional needs of the ablation device, and more particularly, one of ordinary skill will understand that the selection of the components of the exemplary circuit shown in FIG. 2 will be based upon factors such as the frequency of the RF power being used in the system, the type of transducers being used for ablation and the type of sensors that are being used to monitor the transducers. By way of example only, where the RF being used ranges from 3 MHz to 7 MHz, the transducers being used are HIFU, and the sensors being used are thermistors whose resistance varies with temperature from about 1.5 K Ohms to about 7.2 K Ohms, the following criteria may be used to select some of the components: RL1 may be selected in the range of about 72 K Ohms to about 100 K Ohms; RL2 may be selected in the range of about 75 Ohms to about 150 Ohms; each of the capacitors C1, C21, CC1 and CL1 may be selected in the range from about 0.01 uF to about 0.1 uF; each of the capacitors CD1 and CD21 may be selected in the range of about 80 pF to about 200 pF; each of the capacitors CD2 and CD22 may be selected in the range of about 400 pF to about 800 pF; each of the resistors RD1 and RD21 may be selected in the range of about 1M Ohms to about 2M Ohms; and each of the resistors RD2 and RD22 may be selected in the range of about 200K Ohms to about 390K Ohms.

Figure 3:
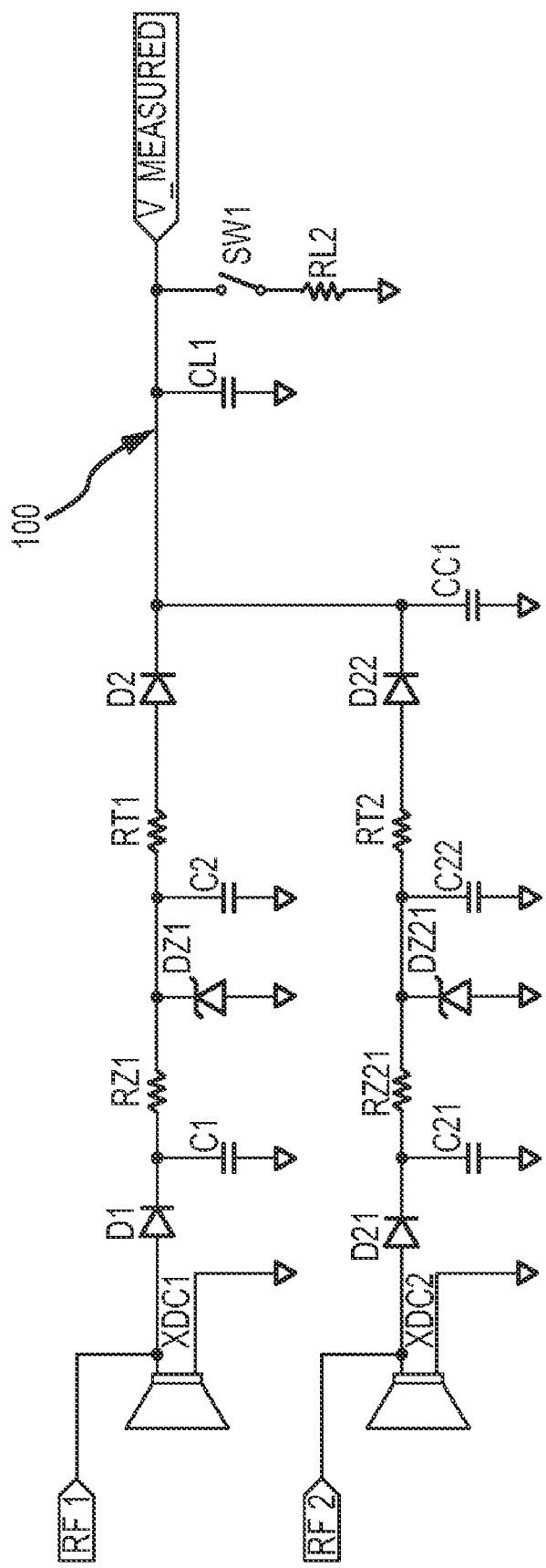
FIG. 3 is circuit diagram for yet another embodiment of the present invention.

While the circuit in FIG. 3 depicts only two transducers (XDC1 and XDC2) sharing a common subchannel, the circuit may be extrapolated to include any number of transducers. Only one transducer is powered at any given time, regardless of whether the circuit contains two or more transducers. While the operation of the circuit will be described in connection with transducer XDC1, the same functional description will apply equally to transducer XDC2—or any other transducer that may be added to the subchannel. For ease of description, however, the functionality will be discussed only in conjunction with transducer XDC1. Based on this description, it will be understood that if RF power is delivered to transducer XDC2 instead of XDC1, the control system would provide information on sensor RT2.

When an RF energy source (not shown) is connected to RF port RF1, high frequency energy is delivered to the transducer XDC1. Diode D1 rectifies the RF signal, and capacitor C1 serves as a low pass filter to provide a low frequency voltage supply. The resulting signal is then subjected to the combination of resistor RZ1 and zener diode DZ1, which together serve as a voltage regulator provided the input voltage exceeds the voltage necessary to cause zener diode DZ1 to reverse bias. The output of the voltage regulator is then low pass filtered by capacitor C2, and the resulting filtered power supply voltage is delivered to sensor RT1. Preferably, the circuit includes an additional diode D2 to serve as a protection device that prevents passage of signals that may be on the subchannel 100 by virtue of the operation of other transducers.

In operation, the voltage that is stored by capacitor C2 is relatively independent of the RF voltage amplitude, provided the RF amplitude is high enough to result in reverse breakdown of zener diode DZ1—which will effectively cause zener diode to operate as a voltage regulator.

In this embodiment, the control system can make a measurement under a single loading condition to determine the temperature of sensor RT1. Switch SW1 may be closed, and the voltage measured across resistor RL2 will ultimately depend upon the ratio of the resistance of resistor RL2 to the sum of the resistances of resistors RL2 and RT1. Preferably the resistance of RL2 is chosen such that it is significantly less than the resistance of RT1, and more preferably, the resistance of RL2 is no more than about 1/10 of the resistance of RT1.

Switch SW1 could be eliminated, but keeping it open most of the time, except during the brief measurement period, is useful to prevent RT1 from self-heating.

In this embodiment, like the others, a capacitor CL1 may be physically located at or near the control system and to help filter any RF interference that may have been picked up on the subchannel 100. Preferably, a second capacitor CC1 is used on the opposite end of subchannel 100, at or near the point where the outputs of the various sensors are joined to the common subchannel 100, to also assist in removing interference on the subchannel 100.

Using this single loading condition, the control system is able to determine the current passing through sensor RT1 by dividing the measured voltage by the resistance of RL2. Having determined the current passing through sensor RT1, the control system can calculate the resistance of sensor RT1 using the known voltage that is being delivered to the sensor RT1. The resistance can then be used to determine the temperature at or near the transducer.

Preferably, the sensor RT1 is a thermistor, which generally has a predictable relationship between resistance and temperature. It is contemplated by the present invention that other known sensors may be used provided there is a known relationship between the resistance of the device and its temperature.

While FIG. 3 depicts one type of voltage regulator, one of skill can appreciate that other voltage regulators may be used in this circuit without deviating from the teachings herein. For example a two terminal voltage regulator may be used. Voltage regulators are often specified based on their voltage outputs as well as the percentage by which the voltage output may vary from device to device.

While FIG. 3 presents an exemplary detection circuit, one of skill will appreciate that other circuits may be used, including additional diodes, capacitors and resistors.

Further, one of skill in the art will be able to select the components based upon the functional needs of the ablation device, and more particularly, one of skill will understand that the selection of the components of the exemplary circuit shown in FIG. 3 will be based upon factors such as the frequency of the RF power being used in the system, the type of transducers being used for ablation and the type of sensors that are being used to monitor the transducers. By way of example only, where the RF being used ranges from 3 MHz to 7 MHz, the transducers being used are HIFU, and the sensors being used are thermistors whose resistance varies with temperature from about 1.5 K Ohms to about 7.2 K Ohms, the following criteria may be used to select some of the components: RL2 may be selected in the range of about 72 Ohms to about 700 Ohms; each of the resistors RZ1 and RZ21 may be selected in the range of about 200 Ohms to about 1K Ohms; and each of the capacitors C1, C21, C2, C22, CC1 and CL1 may be selected in the range from about 0.01 uF to about 0.1 uF.

An additional embodiment of the present invention will now be described in connection with the electrical circuit depicted in FIG. 4. In this embodiment, the circuit of FIG. 1 or 2 may be modified to permit the use of a variable frequency power supply such that the system may use frequency to selectively activate a particular transducer.

The ablation device of this embodiment preferably consists of a plurality of transducers that deliver ablation energy, with the plurality of transducers being divided into multiple subsets such that each subset of transducers shares a common communication buss (or "subchannel"). FIG. 4 represents the circuit for one such subset of transducers. Again, the circuit of FIG. 4 may be replicated for each subset of transducers that shares a common subchannel.

Figure 4:
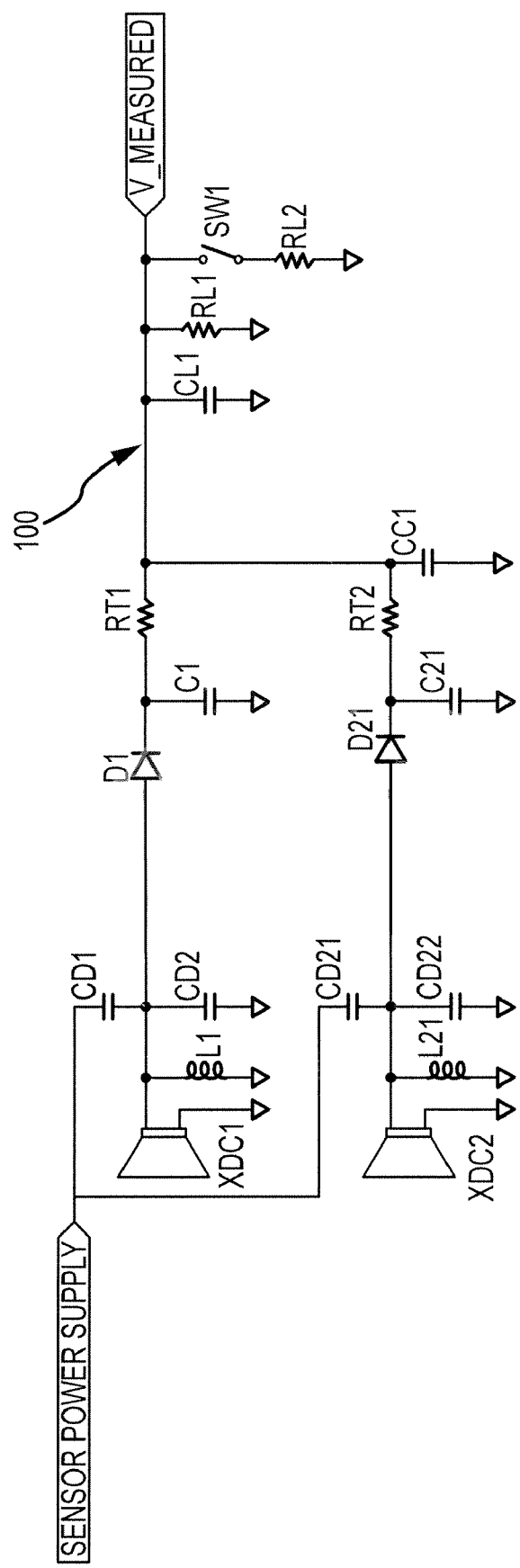
FIG. 4 is circuit diagram for still another embodiment of the present invention.

While the circuit in FIG. 4 depicts only two transducers (XDC1 and XDC2) sharing a common subchannel, the circuit may be extrapolated to include any number of transducers. Only one transducer is powered at any given time, regardless of whether the circuit contains two or more transducers. While the operation of the circuit will be described in connection with transducer XDC1, the same functional description will apply equally to transducer XDC2—or any other transducer that may be added to the subchannel. For ease of description, however, the functionality will be discussed only in conjunction with transducer XDC1. Based on this description, it will be understood that if RF power is delivered to transducer XDC2 instead of XDC1, the control system would provide information on sensor RT2.

In this embodiment, a frequency-selective power converter is used to selectively power certain transducers, simply by changing the frequency of the power supply. Each transducer is paired with a resonant frequency tank with components selected such that no more than one transducer is activated on any subchannel. The RF power supply is tuned to the resonant frequency of a particular frequency tank that will activate the power supply coupled thereto.

To illustrate this concept, inductor L1 and capacitor CD2 serve as a frequency tank, whose resonant frequency will depend upon the inductance of L1 and the capacitance of CD2. When an RF power supply is tuned to the resonant frequency of the frequency tank, the tank resonates and power is delivered via diode D1 to capacitor C1. Diode D1 rectifies the RF signal, and capacitor C1 serves as a low pass filter to provide a low frequency voltage supply. The voltage stored on capacitor C1 is delivered to sensor RT1.

When the power supply is tuned to the resonant frequency of the tank, only the sensor associated with that tank will have sufficient supply voltage to transmit voltage and current.

The low frequency signal is preferably further filtered using capacitor CL1 which is physically located at or near the control system and serves to help filter any RF interference that may have been picked up on the subchannel 100. Preferably, a second capacitor CC1 is used on the opposite end of subchannel 100, at or near the point where the outputs of the various sensors are joined to the common subchannel 100, to also assist in removing interference on the subchannel 100.

The control system is configured to make multiple measurements, including measurements under at least two separate loading conditions. With switch SW1 open, the control system measures the output voltage 120. In this loading condition, resistor RL1 and the resistance associated with sensor RT1 serve as a voltage divider. Preferably the resistance of resistor RL1 is substantially greater than the resistance of sensor RT1, and more preferably the resistance of resistor RL1 is at least 10 times greater than the resistance of sensor RT1. Provided the resistance of resistor RL1 is significantly greater than the resistance of sensor RT1, then the measured output voltage approximates the voltage being delivered to the sensor. This measured output voltage may then be used to help characterize the amount of RF energy being delivered to transducer XDC1.

The control system then measures the output voltage under a second loading condition, namely, with the switch SW1 closed. Once switch SW1 is closed, then resistor RL1 is placed in parallel with resistor RL2. Preferably, the resistance of resistor RL2 is substantially less than the resistance of resistor RL1, and more preferably the resistance of resistor RL2 is no more than 1/10 of the resistance of sensor RT1. If the resistance of resistor RL2 is substantially greater than the resistance of resistor RL1, then the measured voltage may be used in connection with the known resistances of resistors RL1 and RL2 to estimate the current that is passing through sensor RT1 using Ohm's Law (V=I*R).

Using these two loading conditions, the control system is able to determine the voltage being applied to the sensor RT1 using the open switch condition (which voltage level may also be used to characterize the ablation power being delivered to the transducer XDC1), as well as the current that is passing through sensor RT1 using the closed switch condition. Using Ohm's law, the resistance associated with the sensor RT1 can be calculated, and in turn, used to determine the temperature at or near the transducer.

Preferably, the sensor RT1 is a thermistor, which generally has a predictable relationship between resistance and temperature. It is contemplated by the present invention that other known sensors may be used provided there is a known relationship between the resistance of the device and its temperature.

The present invention is useful with ablation devices such as those described in U.S. patent application Ser. No. 11/646,526, which application is incorporated by reference herein as if the application had been set forth herein in its entirety. Disclosed in that application is an ablation device having a plurality of ablation elements on a flexible framework that is designed to encircle body parts, including, for example, encircling a pulmonary vein.

The ablating elements are preferably controlled by a control system. A plurality of temperature sensors on the device are coupled to the control system for use as now described. The control system may control ablation in a number of different ways. For example, the control system may activate one or more pairs of adjacent cells to form continuous lesions between the adjacent cells. After ablation at the one or more adjacent cells, another pair of adjacent cells is activated to form another continuous ablation segment. This process is continued until a continuous lesion of the desired geometry is produced.

To utilize the advantages of the present invention, the ablation device disclosed in U.S. patent application Ser. No. 11/646,526 would be modified to group the plurality of ablation elements into at least two subsets, and each of the subsets would share a common electrical buss or subchannel. Organizing the ablation elements in this fashion would eliminate the need for a separate subchannel for each ablation element, thereby reducing the number of parts and enabling a reduction in size of the device.

Figure 5:
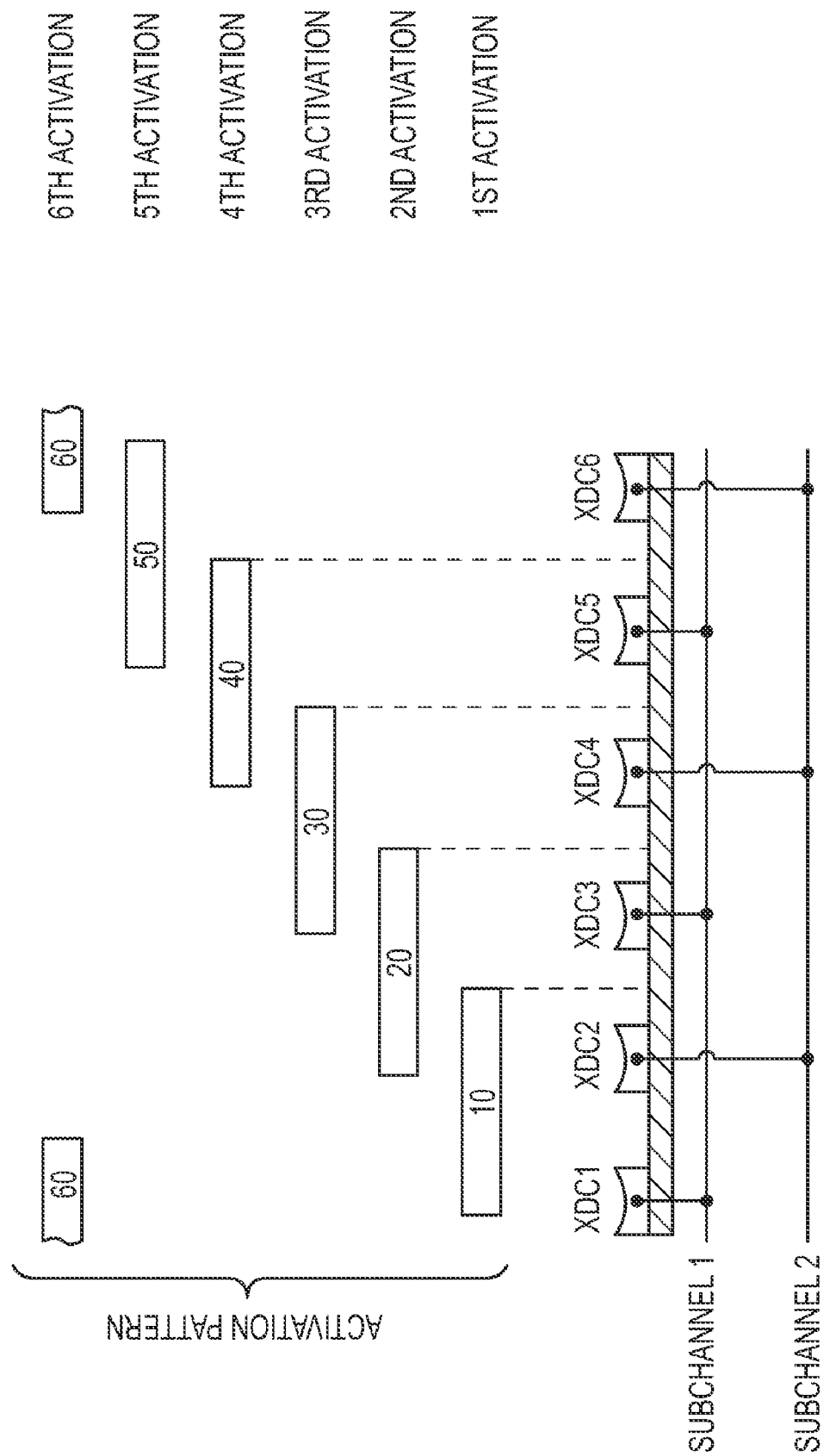
FIG. 5 is a schematic diagram to help explain how the present invention may reduce the number of subchannels for an ablation device.

FIG. 5 illustrates how such a device may be modified and used in an ablation process. FIG. 5 illustrates an ablation device having six transducers, XDC1, XDC2, XDC3, XDC4, XDC5 and XDC6. While a larger or smaller number of transducers may be used in an ablation device, and indeed, the number of elements is often determined by the size of the lesion needed to be created, six is used in FIG. 5 for illustration purposes only.

In FIG. 5, the six ablation elements are divided into two subgroups of three. Transducers XDC1, XDC3 and XDC5 are coupled to subchannel 1, while transducers XDC2, XDC4 and XDC6 are coupled to subchannel 2. One of skill would appreciate that the coupling of the transducers would be accomplished, for example, by using one of the embodiments discussed above in connection with one of FIGS. 1, 2, 3 and 4. This coupling permits the transmission of information on the operation of activated transducers across the subchannels 1 and 2, again, in accordance with the discussions above. While a greater number of subgroups could be utilized (and hence, a greater number of subchannels), FIG. 5 discloses two subchannels for illustration purposes. Using the methodology of the present invention, the number of transducers that may be activated at once may also be varied; indeed, the number of elements activated at any one time may vary from 1 up to the number of subchannels available to transmit operational information. By way of example, if there are three subgroups, and hence 3 subchannels, then the transducers may be activated one at a time, two at a time, or three at a time.

The ablation device of FIG. 5 is controlled by a control system (not shown in FIG. 5), similar to one disclosed above. For illustration purposes, the ablation elements are activated in successive pairs (which may be described as a sliding pair fashion). As illustrated, the first activation 10 energizes transducers XDC1 and XDC2. The second activation 20 energizes transducers XDC2 and XDC3. The third activation 30 energizes transducers XDC3 and XDC4. The fourth activation 40 energizes transducers XDC4 and XDC5. The fifth activation 50 energizes transducers XDC5 and XDC6. The sixth activation 60 energizes transducers XDC6 and XDC1. In each of the six activation stages, only one transducer per subchannel is activated. The ultimate functionality of the ablation device has not changed, but the device incorporating the present invention has fewer subchannels than would be expected.

When ultrasound transducers are used, they are preferably operated while varying one or more characteristics of the ablating technique such as the frequency, power, ablating time, and/or location of the focal axis relative to the tissue. In a first treatment method, the transducer is activated at a frequency of about 2 MHz to about 7 MHz, preferably less than about 3.5 MHz, and a power of about 80 to about 150 watts, preferably about 130 watts, in short bursts. For example, the transducer may be activated for about 0.01 seconds to about 2.0 seconds and preferably for about 1.2 seconds. The transducer is inactive for about 2 seconds to about 90 seconds, more preferably for about 5 seconds to about 80 seconds, and most preferably for about 45 seconds between activations.

In this manner, a controlled amount of accumulated energy can be delivered to the tissue in short bursts to heat tissue at and near the focus while minimizing the impact of blood cooling at the FS. Ablation at this frequency may continue until a controlled amount of energy is delivered, such as about 0.5 kilojoule to about 3 kilojoules. Treatment at this frequency in relatively short bursts produces localized heating at the focus. At the first frequency, energy is not absorbed as quickly in the tissue as it is at higher frequencies, so that heating at the focus is not significantly affected by absorption of ultrasound energy in tissue before reaching the focus.

In a second treatment method, the ultrasound transducers are operated for longer periods of time, preferably about 1 second to about 4 seconds and more preferably about 2 seconds, to distribute more ultrasound energy between the focus and the near surface. The frequency during this treatment is also about 2 MHz to about 14 MHz, more preferably about 3 MHz to about 7 MHz and preferably about 6 MHz. The transducer is operated for about 0.7 seconds to about 4 seconds at a power of about 20 to about 80 watts, preferably about 60 watts. The transducer is inactive for at least about 3 seconds to about 60 seconds, more preferably for about 40 seconds between each activation. In this manner, a controlled amount of energy can be delivered to heat tissue between the focus and the transducer. The treatment at this frequency may continue until a controlled amount of total energy is delivered, such as about 750 joules.

In a third treatment method, the ultrasonic transducers are activated at a higher frequency to heat and ablate the near surface. The transducer is preferably operated at a frequency of between about 3 MHz and about 16 MHz, and preferably at least 6 MHz and most preferably about 16 MHz. The transducer is operated at lower power than the first and second treatment methods since ultrasound is rapidly absorbed by the tissue at these frequencies so that the near surface is heated quickly. In a preferred method, the transducer is operated at about 2 to about 20 watts and more preferably about 15 watts. The transducer is preferably operated for a sufficient duration to ablate tissue, such as about 20 seconds to about 80 seconds, and preferably about 40 seconds. Often, the near surface ("NS") temperature will reach about 70 degrees C. to about 85 degrees C.

In general, the treatment methods described above deliver energy closer and closer to the near surface NS with each subsequent treatment method. Such a treatment method is conducted using a fewer number of subchannels, and this methodology may be practiced with other devices without departing from this aspect of the invention and, as mentioned below, may be automatically controlled by the control system.

The device preferably has a number of cells with each cell having at least one ablating element.

After ablating tissue with all of the cells, gaps may exist between adjacent ablations. The tissue in the gaps is preferably ablated by moving at least one of the ablating elements. In one method, the entire device is shifted so that each cell is used a second time to ablate one of the adjacent gaps. Yet another method of ablating tissue in the gaps is to tilt one or more of the ablating elements to direct the ultrasound energy at the gaps between cells. The ablating element may be moved, tilted or pivoted in any suitable manner and is preferably tilted with an inflatable membrane. The transducer may also simply be configured to direct ultrasound energy to tissue lying beneath the gaps between adjacent transducers. In this manner, the device does not need to be moved or tilted.

The device may be adhered to tissue with suction although suction is not required. The device may also have a membrane filled with a substance that transmits the ultrasound energy to the tissue. The membrane conforms to the tissue and eliminates air gaps between the device and tissue to be ablated. Alternatively, the device may have a solid element that contacts the tissue and transmits the ultrasound energy to the tissue. The device may also be used with a gel applied to the tissue that transmits the ultrasound energy and eliminates air gaps.

The device may also have a number of ultrasound transducers with varying characteristics. For example, the device may have cells that provide focused ultrasound having different focal lengths or that are intended to operate at different frequencies or power. In this manner, the user may select the appropriate cell to ablate a particular tissue structure. For example, it may be desirable to select an ablating element with a small focal length and/or low power when ablating thin tissue.

The ablating device is preferably automatically operated by the control system to perform an ablation procedure. The ablating device may be any suitable ablating device that produces focused ultrasound such as those described herein that are specifically incorporated here. The ablating devices are introduced into the chest and placed at an epicardial location where cardiac tissue is to be ablated. Ultrasound energy is then delivered at a first frequency for a first plurality of time periods such as 3-7 or 4-5 pulses. The ultrasound energy is then deactivated for at least 20 seconds and preferably about 51 seconds between each activation at the first frequency. Ultrasound energy is then delivered at a second frequency, which may be higher than the first frequency, for a second plurality of time periods.

The ultrasound energy is then deactivated for at least 10 seconds and preferably about 38 seconds. In one aspect, the pulse duration is longer during delivery at the second frequency than the first frequency. In still another aspect, ultrasound energy is delivered during a third period of time at a power lower than the power at the first and second frequencies and may be at a frequency higher than the first frequency. In yet another aspect, the ultrasound energy is delivered at the first frequency in pulses for a total of about 4-8 seconds and at the second frequency for a total of about 6-10 seconds.

If the number of subsets (and hence the number of subchannels) were to be adjusted, a different ablation activation pattern could easily be generated to take advantage of the teachings of this document. The controller is preferably configured to activate no more than one transducer at a time for each subset. Generally, if the total number of transducers is divided into N subsets, then the device should have at least N subchannels for transmitting electrical information, with each of the N subchannels being coupled to a respective subset of the N subsets of transducers.

The control system of the present invention may be used to conduct a thermal response analysis of the tissue to be ablated to determine the appropriate ablation technique. The tissue to be ablated is heated, or cooled, and the temperature response of the tissue over time is recorded. The temperature response is then analyzed to determine the appropriate ablation technique. The analysis may be a comparison of the temperature response against a database of temperature responses or may be a calculation that may require user input as described below.

The ablation at each cell may be controlled based on temperature measured at the temperature sensors. For example, the control system may be configured to maintain a near surface NS temperature of about 0 to about 80 degrees C., more preferably about 20 to about 80 degrees C., and most preferably about 40 to about 80 degrees C. The temperature can be adjusted by changing the fluid flow rate and temperature and/or the power delivered to the ablating element. The control system may also have a multiplexer that delivers energy to only the cells having a temperature below the threshold temperature. Alternatively, the multiplexer may deliver energy to only the coldest cells or only a number of cells that register the coolest temperatures.

The control system may also be configured to measure a temperature response of the tissue to be ablated. The temperature response of the tissue is measured to provide a tissue characterization that can be used to select the appropriate ablation technique. The ablation technique is primarily selected to produce a temperature of at least about 50 degrees C. at the far surface ("FS") of the tissue. When ablating cardiac tissue, for example, the control system determines the ablation technique required to form a transmural lesion that requires a far surface FS temperature of about 50 to about 80 degrees C. and more preferably about 50 to about 60 degrees C. Measuring temperature at the far surface FS is somewhat difficult so the temperature of the near surface NS is used in conjunction with the methods and devices described herein. Of course, the temperature of the far surface FS may be measured to determine when the ablation is complete rather than using the temperature response described below.

The temperature response of the tissue may be performed in the following manner. The tissue to be ablated is heated or cooled and the temperature response over time is measured with the temperature sensors. The temperature response over time at the near surface NS provides a rough indication of the thermal properties of the tissue to be ablated. The thermal properties of the tissue is affected by a number of variables including tissue thickness, amount of fat and muscle, blood flow through the region and blood flow and temperature at the far surface FS. These factors all play a role in the temperature response of the tissue. The tissue thickness, for example, affects the temperature response in the following manner. When a thin tissue layer is heated, the temperature at the near surface will generally increase more slowly than with a thick layer since the flow of blood at the far surface will draw heat away quicker with the thin tissue layer. The control system preferably measures the temperature response for at least two temperature sensors for each ablating element with one of the temperature sensors being positioned laterally spaced to measure the temperature change at adjacent portions of the tissue.

After measuring the temperature change over time, the temperature response is then analyzed to determine the appropriate ablation technique. The analysis may be a comparison of the temperature response with temperature response curves of known tissue types. The temperature response curves may be developed empirically or may be calculated. The temperature response may also consider other variables input by the user including blood temperature and flow rate and the presence and amount of fat. When assessing the temperature response during heating with the ablating element, the amount of energy delivered to the tissue may also be taken into account in characterizing the tissue.

Using the results of the temperature response assessment, the control system 334 determines the appropriate ablation technique to produce the desired far surface FS temperature. In one mode of operation, the control system determines the amount of time required to reach a desired far surface FS temperature when the near surface NS is maintained at a temperature of less than about 60 degrees C. The control system preferably maintains an adequate flow rate and temperature of the flowable material to maintain the desired near surface NS temperature. The control system monitors the temperature of the near surface NS with temperature sensors. After the calculated amount of time has elapsed, the control system automatically stops delivering ablating energy. Alternatively, the ablation may take place until the near surface NS reaches a target temperature as sensed by the temperature sensors. The continuity of the ablation may then be checked in any manner described herein.

In use, the ablation device of the present invention may be wrapped around a structure, such as the pulmonary veins, with the locking mechanism to form a closed loop. The vacuum source may then be activated to adhere the cells to the epicardium. Manual pressure can be applied to cells that are not sufficiently adhered to the tissue. The control system may then ablate tissue while delivering fluid to cool the tissue and conduct RF energy to the tissue. The continuity of ablation is then assessed by any suitable method including those described herein.

The control system may be designed to automatically ablate in any manner described herein. For example, the control system can change the frequency, power, focal length and/or operating time to provide the desired ablating technique. The change in frequency and power may be completely automatic or may require some user input such as visual indications of fat and/or tissue thickness. For example, the control system may be designed to automatically sequence through two or more different ablating techniques such as those described above. Other techniques, of course, may be used depending on the tissue characteristics and the type and characteristics of the one or more ultrasound transducers. The control system may also utilize feedback, such as temperature-based feedback or electrical impedance, to actively control the ablations. Furthermore, although various methods have been described, the corresponding functionality of the control system is provided. Thus, all methods of the present invention provide corresponding devices and systems as controlled by the control system.

Although several embodiments of this invention have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of using a common subchannel to assess operating characteristics of one of a plurality of transducers that are coupled to said subchannel, said method comprising:
    providing a plurality of transducers and a plurality of sensors, each of the plurality of transducers having one of the plurality of sensors coupled thereto for determining the temperature of the transducer, and each transducer configured to be selectively powered with RF energy;
    connecting an output of each of the plurality of sensors to a common subchannel, said subchannel having a measurement terminal on one end and a coupling input on the other end, said measurement terminal being configured for connecting to a meter, and said coupling input being configured to be coupled to an output of each of the plurality of sensors;
    connecting an RF power source to a selected one of the plurality of transducers; selectively providing a low frequency power source to the sensor coupled to the selected transducer; and
    measuring at least one voltage on the measurement terminal and using the measured at least one voltage to determine the temperature of the sensor coupled to the selected transducer.

2. The method of claim 1, wherein the step of measuring at least one voltage comprises:
    measuring a first voltage level representative of a voltage that is being applied to the sensor coupled to the selected transducer;
    measuring a second voltage level representative of a current that is flowing through the sensor coupled to the selected transducer;
    calculating a resistance of the sensor using the measured first voltage level and the measured second voltage level; and using a known relationship between temperature and resistance for the sensor to determine the temperature of the sensor.

3. The method of claim 1, wherein the selectively providing step comprises:
rectifying and filtering with a low pass filter the RF power source connected to the selected transducer.

4. The method of claim 1, wherein the selectively providing step comprises: using a voltage divider to condition the RF power source connected to the selected transducer, thereby generating a conditioned signal, and then rectifying and filtering the conditioned signal with a low pass filter to selectively provide a low frequency power source to the selected sensor.

5. The method of claim 1, wherein the step of selectively providing a low frequency power source comprises using a voltage regulator coupled to the RF power source powering the selected transducer to selectively power the sensor.

6. The method of claim 5, wherein the step of selectively providing a low frequency power source further comprises rectifying and filtering with a low pass filter the RF power source connected to the selected transducer.

7. The method of claim 1, wherein each of the plurality of transducers is configured to operate at a different frequency, and wherein the step of selectively providing a low frequency power source comprises using a resonant frequency circuit coupled to the RF power source powering the selected transducer to provide a resonant output, and then rectifying and filtering the resonant output with a low pass filter before delivering the low frequency power source to the selected sensor.

8. The method of claim 1, wherein the step of measuring at least one voltage comprises:
determining a current that is flowing through the sensor coupled to the selected transducer;
calculating a resistance of the sensor using a known voltage level and the measured current; and
using a known relationship between temperature and resistance for the sensor to determine the temperature of the sensor.

9. A method of using a common subchannel to assess characteristics of one of a plurality of transducers that are coupled to said subchannel, said method comprising:
providing a plurality of transducers, each of which may be selectively powered using RF power;
coupling a sensor to each of said plurality of transducers;
connecting an output of each of the sensors to a common subchannel, said subchannel having a measurement terminal on one end and a coupling input on the other end, said measurement terminal configured for connecting an analog meter, and said coupling input configured to be coupled to an output of each of the plurality of sensors;
connecting an RF power source to one of the plurality of transducers;
filtering an output of the RF power source to provide low-frequency power to the sensor coupled to the transducer that is receiving RF power; and
measuring at least one voltage on the measurement terminal and using the measured at least one voltage to characterize an operational state of the sensor.

10. The method of claim 9, wherein the step of measuring at least one voltage comprises:
measuring a first voltage level representative of a voltage that is being applied to the sensor coupled to the transducer that is receiving RF power;
measuring a second voltage level representative of a current that is flowing through the sensor coupled to the transducer that is receiving RF power; and
calculating a temperature of the sensor using the measured first voltage level and the measured second voltage level.

11. The method of claim 10, wherein the step of filtering an output of the RF power source further comprises rectifying the RF power source.

12. An ablation system comprising:
a plurality of transducers, divided into a number N of subsets, N being less than a total number of the plurality of transducers;
a controller configured to activate no more than one transducer at a time in each subset of transducers;
N subchannels for transmitting electrical information, each of the N subchannels being coupled to a respective subset of the N subsets of transducers;
a plurality of detector circuits, each of the plurality of detector circuits being coupled to one of the plurality of transducers, each of the plurality of detector circuits comprising a sensor; and
a measurement device for measuring an analog signal present on one of the N subchannels;
whereby said controller uses an output from the measurement device to assess information being measured by the sensor coupled to a transducer that has been activated by the controller.

13. The system of claim 12, further comprising a switching network to selectively couple one of the N subchannels to the measurement device for measurement.

14. The system of claim 12, wherein the measurement device measures at least two voltages on the subchannel to characterize an operational state of the sensor.

15. The system of claim 14 wherein the system:
measures a first voltage level representative of a voltage that is being applied to the sensor coupled to the activated transducer;
measures a second voltage level representative of a current that is flowing through the sensor coupled to the activated transducer; and
calculates a temperature of the sensor coupled to the activated transducer using the measured first voltage level and the measured second voltage level.

16. A measurement system for monitoring a plurality of transducers using a common measurement subchannel, said measurement system comprising:
a plurality of transducers, each of which is coupled to an RF power source;
an RF controller to control the delivery of RF power to the plurality of transducers, configured such that no more than one of the plurality of transducers is powered at any point in time;
a plurality of detector circuits coupled to the plurality of transducers, whereby each of the plurality of detector circuits is associated with one of the plurality of transducers, each of the plurality of detector circuits comprising:
a rectification circuit to rectify an RF power signal applied to the coupled transducer;
a low pass filter to filter the rectified signal;
a sensor; and
an output port to present a low frequency detected signal as measured relative to the sensor;
a common measurement subchannel coupled to each output port of the plurality of detector circuits;

a measurement selection circuit to measure characteristics of a low frequency detected signal on the measurement subchannel, said measurement selection circuit comprising:
- a first measurement resistor, said first measurement resistor having a resistance value that is at least about 10 times greater than a resistance value of a sensor in each of the plurality of detector circuits;
- a second measurement resistor in series with a switch, said second measurement resistor having a resistance value that is less than about $\frac{1}{10}$ of the resistance value of the first measurement resistor, whereby said first measurement resistor is configured to be in parallel with the second measurement resistor when the switch is activated; and
- a measurement selection controller to open and close said switch;

whereby the measurement system monitors at least a voltage on the common measurement subchannel that is used to characterize the voltage applied to the powered transducer.

17. The system of claim 16, wherein each of the sensors in the plurality of detector circuits is a thermistor,
wherein each of the sensors has an effective resistance value of about RT1, and wherein the first measurement resistor has a resistance value of at least about 10 times RT1,
whereby the sensor and the first measurement resistor form a voltage divider to permit the measurement system to monitor a voltage across the first measurement resistor when RF power is delivered to the powered transducer.

18. The system of claim 17 wherein each of the sensors in the plurality of detector circuits is a low resistance thermistor, and wherein the measurement controller includes a processor that is programmed to:
measure a first voltage level on the common measurement subchannel with the switch open, said measured first voltage level being representative of the amplitude of the RF voltage applied across the powered transducer;
measure a second voltage level with the switch closed, said controller using the measured first voltage level, the measured second voltage level, and the known effective resistance of the parallel combination of the first measurement resistor and the second measurement resistor to calculate a temperature of the sensor in the detector circuit associated with the powered transducer.

19. The system of claim 18, wherein the common measurement subchannel has a measurement terminal on one end and a coupling input on the other end, said measurement terminal configured for connecting a voltage reader, and said coupling input configured to be coupled to each output port of the plurality of detector circuits, said common measurement subchannel further comprising: a low pass filter physically coupled to the measurement subchannel at or near the measurement terminal.

20. The system of claim 18, wherein the common measurement subchannel has a measurement terminal on one end and a coupling input on the other end, said measurement terminal configured for connecting a voltage reader, and said coupling input configured to be coupled to each output port of the plurality of detector circuits, said common measurement subchannel further comprising: a low pass filter physically coupled to the measurement subchannel at or near the coupling input.

21. The system of claim 18, wherein each of the plurality of detector circuits further comprises:
a voltage divider located on a front end of the low pass filter.

22. The system of claim 21, wherein the voltage divider comprises two resistors.

23. The system of claim 21, wherein the voltage divider comprises two capacitors.

24. The system of claim 18, wherein each rectification circuit comprises a diode.

25. The system of claim 18, wherein each rectification circuit comprises two or more diodes.

26. The system of claim 18 wherein the sensor is a thermistor.

27. The system of claim 18 wherein the sensor comprises a device that has a known relationship between temperature and resistance.

* * * * *